United States Patent [19]

Shestopalov et al.

[11] 4,422,778

[45] Dec. 27, 1983

[54] METHOD FOR MEASURING ASPHALT PAVEMENT TEMPERATURE AND DEVICE FOR IMPLEMENTATION OF THE SAME

[76] Inventors: Alexandr A. Shestopalov, prospekt Smirnova, 20, korpus 1, kv. 30; Ernst I. Denikin, Grazhdansky prospekt, 13, korpus 1, kv. 190; Nikolai Y. Kharkhuta, prospekt Smirnova, 37, korpus 1, kv. 20, all of, Leningrad; Alexandr A. Vasiliev, Volzhsky bulvar, 40, kv. 36, Moscow; Vyacheslav I. Okunev, ulitsa Schepkina, 12, kv. 47, Rybinsk, all of U.S.S.R.

[21] Appl. No.: 213,616

[22] Filed: Dec. 5, 1980

[51] Int. Cl.³ .................. G01K 13/02; G01N 25/72
[52] U.S. Cl. .................................... 374/135; 73/146; 374/4; 374/143
[58] Field of Search ............... 73/349, 343 R, 146, 73/38, 357, 146.3, 37; 374/120, 135, 143

[56] References Cited

U.S. PATENT DOCUMENTS

| 773,684 | 11/1904 | Speller | 73/357 |
|---|---|---|---|
| 1,062,348 | 5/1913 | McDonnell, Jr. | 374/120 |
| 1,949,355 | 2/1934 | Cline | 73/343 R X |
| 2,582,859 | 1/1952 | Centofanti | 73/40 X |
| 2,645,117 | 7/1953 | Bendix et al. | 73/49.2 |
| 2,688,876 | 9/1954 | Barnes | 73/343 R |
| 2,737,050 | 3/1956 | Moninger | 73/343 R |
| 2,964,947 | 12/1960 | DeLong | 73/343 R |
| 3,138,014 | 6/1964 | Jorre | 73/38 |
| 3,184,957 | 5/1965 | Ellis et al. | 73/38 |
| 3,296,865 | 1/1957 | Blackshear, Jr. et al. | 73/349 |
| 3,341,706 | 9/1967 | Swift et al. | 73/146 X |
| 3,383,913 | 5/1968 | Swift | 73/146 |
| 3,533,288 | 10/1970 | Franck | 73/343 R |
| 3,625,049 | 12/1971 | Mills et al. | 73/49.2 |
| 3,691,840 | 9/1972 | Dufour et al. | 374/135 |
| 3,861,196 | 1/1975 | Domenighette | 73/38 |
| 3,940,988 | 3/1976 | Reed | 73/349 |
| 4,199,985 | 4/1980 | Tafumi et al. | 374/120 |

FOREIGN PATENT DOCUMENTS

| 51477 | 7/1937 | U.S.S.R. |
| 52094 | 11/1937 | U.S.S.R. |
| 77795 | 12/1949 | U.S.S.R. |
| 251870 | 2/1970 | U.S.S.R. |

OTHER PUBLICATIONS

Publ., "Effect of Process and Mechanization Means on Quality of Asphalt Concrete Road Pavement Production," by Badalov et al., Leningrad House of Technology, pp. 20–21, (FIG. 6), 1977.

Primary Examiner—Daniel M. Yasich
Attorney, Agent, or Firm—Robert E. Burns; Emmanuel J. Lobato; Bruce L. Adams

[57] ABSTRACT

A method for measuring the temperature of an asphalt pavement, that comprises the measurement of temperature of air used as a heat-carrying agent, drawn through the pavement prior to measuring the temperature thereof. The air is drawn through the pavement by application of a vacuum to a pavement area isolated from the environment. A device used for the implementation of the method comprises a hollow, thermally isolated chamber with open end faces. Installed on one of its end faces is a means used for providing the air filtration through the pavement and made as an exhaust blower whose impeller is arranged inside the chamber in close vicinity to its end face.

4 Claims, 4 Drawing Figures

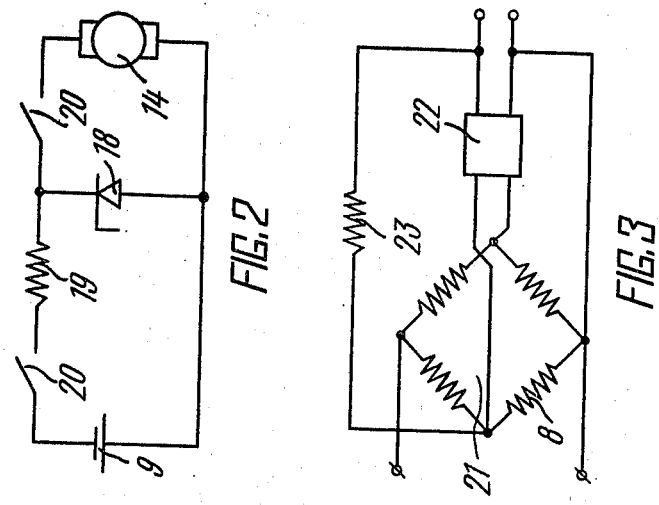
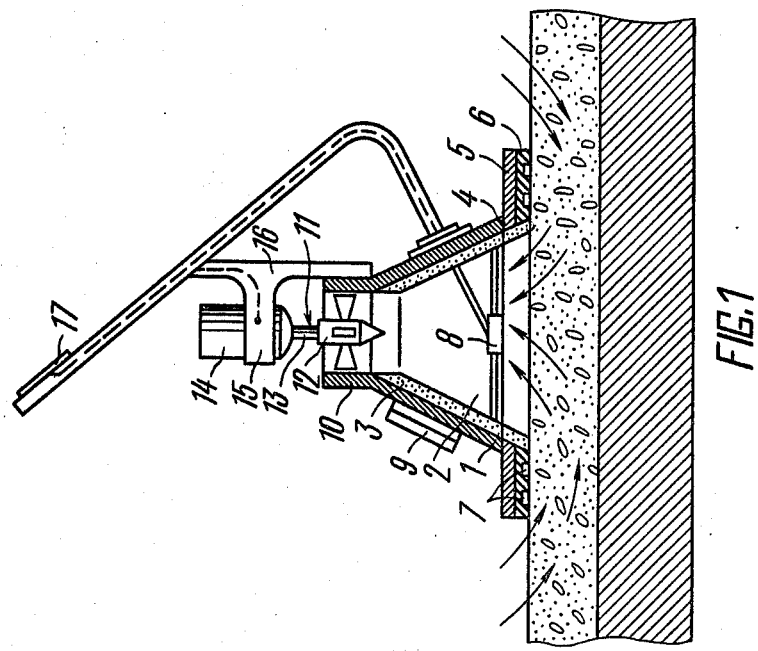

METHOD FOR MEASURING ASPHALT PAVEMENT TEMPERATURE AND DEVICE FOR IMPLEMENTATION OF THE SAME

FIELD OF THE INVENTION

The present invention relates to highway engineering, and more particularly, to methods and devices for measuring the temperature of an asphalt pavement. Most successfully, the present invention can be used in building of roads with an artificial pavement made preferably from a hot or warm asphalt. Furthermore, the method and the device can find application for determination of average temperatures inside items made from a porous material in other branches of science and technology.

BACKGROUND OF THE INVENTION

Among a number of factors defining the quality of a road with an asphalt pavement, the main ones are the compactness and the strength of the latter or, more exactly, of the structural layers made therefrom. If the strength of the pavement is chiefly defined by a number of processing factors implemented in course of the asphalt concrete preparation, the pavement compactness results only from the treatment of the already finished paving asphalt mixture directly on the road, that is from the mechanical compaction process. The aim of the mechanical compaction is, as a rule, to produce a material with a low degree of porosity that is a basic characteristic defining, together with the physical strength of the road pavement material, its endurance in service. If the porosity exceeds the tolerable limits, this will lead to a quick destruction of the pavements under the conditions of sharply varying climatic conditions, especially in northern latitudes, and will require additional expenditures for its repair. The cause of pavement destruction is moisture getting into pores in the pavement, that changes its volume depending upon the temperature and, thus, produces, except the service loads, additional internal loads on the pavement, stresses that are often practically the only cause of its destruction.

As soon as the minimum pavement porosity is achieved as well as its maximum strength depending, to a certain degree also upon the porosity, one tries to select such compaction conditions that stresses produced by compaction machines in the paving asphalt mixture laid into the road basement be in a certain relationship with the ultimate strength of this mixture. This relationship is $\tau = 0.94 - 0.98 \tau_{us}$, where $\tau$—current value of stress produced in the paving mixture and $\tau_{us}$—ultimate strength of the paving mixture.

Another very important factor for which allowance is made in the paving mixture compaction is that the mixture is laid onto the road base or bed at a temperature of 140° to 160° C., but this temperature decreases down to the ambient temperature in course of compaction. The temperature decrease is exponential. In the light of the aforesaid the compaction process appears to be very labour-consuming because $\tau_{us}$ varies its value with temperature, and this means that $\tau$ should be continuously changed following the variation of $\tau_{us}$ in accordance with the above relationship. In other words, the load applied to the paving mixture in course of its compaction should be also varied exponentially, increasing continuously. Reasonable paving asphalt mixture temperatures within which the compaction is accomplished are from 130° C.–150° C. to 70° C.–60° C.

When modern compaction rollers are being developed for pavement made from hot or warm asphalt, one tries to meet to a great extent the requirement to increase gradually the load acting on the cooling mixture. In this connection, a method of pavement compaction is presently adapted that is based on the successive use of several rollers of different weights, from light rollers to heavy ones. Due to this fact it is customary to divide all rollers into three categories depending upon their mass: light—with a mass up to 5T, medium—with a mass from 5 to 10T, and heavy—with a mass over 10T. Although such a division is universally accepted, it is nevertheless incomplete: a deeper mass differentiation is possible within every weight category. So, for example, the light category includes rollers with a mass of 1.5T, 3T, 5T.

In order to implement the above mentioned method it is necessary to have from 3 to 7 and more rollers of various weights. It should be noted that there are already being developed compaction rollers implementing the exponential law of load variation during the compaction, however these rollers at present are practically no more than subjects of laboratory investigations.

The modern asphalt pavement compaction process is simple in itself, but requires the time intervals of operation of rollers of every weight category to be maintained with a high accuracy. For this purpose, the pavement temperature is measured continuously in order to replace the roller of one weight by another one that is more heavy, in due time, to compact the pavement. Really, the pavement temperature is the only objective criterium that can be used in course of compaction of the pavement since the attempt to measure $\sigma_{us}$ is merely impracticable under field conditions, although this parameter allows to judge more objectively the necessity to replace one type of roller by another than the temperature. Nevertheless, the measurement of the latter is most widely used due to its practicability.

Various methods and devices are known allowing determination of the pavement temperature in course of compaction. The contact methods and devices of the type described in the USSR Author's Certificate No. 52,094 is the most simple among them. This method is based on the contact measurement of the heated body surface temperature. The device implementing this method is a thermocouple made as an elastic conical helical spiral having its base secured to a thrust ring.

These method and device are very simple. However, their use results in a considerable error in temperature measurement because of heat exchange between the thermocouple and the environment as well as because of thermal sluggishness. The principal problems are purely technical and are caused first of all by the bitumen sticking to the surface of the sensing member—the thermocouple. Any measures aimed at elimination of this disadvantage would lead to a reduction in the measurement accuracy and to an increase in the radiation heat exchange as well as in the sluggishness. Furthermore, the contact therermometer responds only to the surface temperature that is mostly not equal to the actual, so-called average layer cross-section temperature, i.e. the temperature that shall be taken into account in the asphalt compaction process.

Also known in the prior art are a contact method of soil or asphalt temperature measurement and a device for its implementation that are partially free from the disadvantages inherent in the method and the device discussed hereinabove (cf. USSR Author's Certificate No. 77,795). According to this method the sensing member of the instrument is immersed into the soil or asphalt layer to measure its temperature. The device used to implement this method is a cylinder filled with liquid and provided with a graduated tube communicating with the cylinder and filled with the same liquid. The tube shows the variation of the liquid volume in the cylinder upon heat expansion of the liquid and gives indirect information about the temperature of the soil or asphalt layer into which the cylinder has been immersed.

These method and device are intended for measuring just the average soil or asphalt temperature. However their use requires to immerse the cylinder into the pavement each time the temperature is to be measured, thus disturbing its continuity, to say nothing of the considerable labour required for the immersion itself which should be repeated tens of times during one compaction cycle of 40 to 60 minutes long.

Also known are non-contact methods of measuring the surface temperature of bodies, in particular of the asphalt mixture. Among these most widely used are pyrometric methods. The devices implementing these methods are called pyrometers. In the pyrometric method of temperature measurement the heat radiation of heated objects is measured. Depending upon the nature of information derived the pyrometers can be devided into devices for local measurement of temperature in a given point of the object and devices intended to analyse temperature fields (thermovisors). Depending upon the principle of operation one distinguishes luminous filament, colour and radiation pyrometers. The luminous filament, visual pyrometers are used for measuring luminance temperatures over 600° C. Their principle of operation is based on the dependence of the spectral luminance of the heated bodies on their temperature, described by the planck and Wien laws. The action of the colour pyrometers is based on the comparison of object radiation intenssities in two spectral ranges. The logarithm of their ratio varies inversly with the object colour temperature.

The action of the radiation pyrometers is based on the use of the Stefan-Boltzmann law expressing the relationship between the energy radiated by a body and its temperature. The instruments of this type are widely used for measuring low temperatures (20° to 100° C.), thermocouples and bolometers serving as radiation receivers. Thermopiles (thermocouply connected in series) are frequently used.

Known in particular is a pyrometer used as a rolling monitoring device allowing the temperature of asphalt pavement surface to be measured continuously and remotely (see the book V. V. Badalov et al. "Effect of process and mechanization means on quality of asphalt concrete road pavement production", Leningrad House of Technology (LDNTP), 1977, p. 21). The device is installed on a roller and comprises two units: indicating and measuring. The measuring unit of the device is fastened to the roller frame at a distance of 80 to 100 cm from the asphalt pavement surface. The indicating unit is arranged on the instrument board of the operator's control station. The device is operated from the roller storage battery.

It should be noted that the non-contact methods of temperature measurement described hereinabove and pyrometers used for this purpose and, in particular, the rolling monitoring device are rather complicated and are very expensive. Furthermore, under all circumstances they measure only the surface temperature of bodies while under the working conditions the asphalt surface temperature differs materially from the average layer temperature of from the temperature inside the asphalt layer. In course of compaction the surface of the asphalt layer is always covered with water spots that appear due to the compulsory abudant wetting of roller drums with water. This is done to prevent asphalt sticking to the roller drums. The surface water disturbs the temperature measurement. One is forced either to introduce large corrections into the measurement results or to find surfaces that are not covered with water.

One of the non-contact methods used presently for measuring the object temperature is the method comprising the measurement of temperature of gaseous heat-carrying agent used to blow the surface of this object. Such a method and respective device are described in USSR Author's Certificate No. 251,870.

When applied to the measurement of asphalt pavement temperature the abovementioned method and device possess a number of disadvantages the main of which are insufficient accuracy and reliability. This is caused by the strong effect of the surface condition of the asphalt pavement that is abudantly wetted due to the reasons mentioned hereinabove as well as by the atmospheric conditions, i.e. by the wind and the air temperature. All this requires that the temperature readings determined with the aid of this method be corrected, but the determination of these corrections is difficult.

The method and device adopted as a prototype are to a certain degree free from the disadvantages inherent individually in each method and device used for radiation temperature measurement and its measurement by means of a gaseous heat-carrying agent. This method and the device used for implementing the same are described in USSR Author's Certificate No. 51,477. The essence of this method consists in particular in that the surface temperature of the soil and other similar materials is determined from the temperature of a heat-conducting casing accommodating a radiation energy indicator and from that of the air enclosed within the casing at the instant the radiation heat exchange balance is established between the surface being measured and the parts of the measuring device. At junctions of the radiation energy indicator, for example a thermopile, included into a certain system with other bodies the radiation energy balance should be zero if all bodies of the system have the same temperature. This follows directly from the Kirchhoff's law. The method is implemented by a device comprising a metallic massive casing open on one side and provided with a heating winding of high-resistance wire. The casing is covered with thermal insulation, and a mercurial thermometer is arranged therein. Accommodated inside the casing is a radiation energy indicator sensing the radiation of the surface being investigated. This indicator is connected electrically with a galvanometer and closed with a special window made from rock-salt or fluorite whereas the casing is silver plated inside.

The method and the device mentioned hereinabove increase slightly the temperature measurement accuracy as compared with those discussed above since in this event the effect of environmental, in particular atmospheric factors is avoided.

However the accuracy and reliability of temperature measurements with the use of this method do not meet the requirements of the modern asphlat compaction process.

Really, the moisture on the pavement surface will materially change the radiation. In other words, the radiation intensity will continuously vary depending upon the variation of pavement wetness the constancy of which can be practically never guaranteed. Furthermore, said method and device, give no idea about the temperature inside the pavement layer, but this is that in which the technologists performing the compaction are interested.

Thus, the confidence of the obtained temperature measurement rasults will be low. Worthy of notice is also the complexity of the device itself which comprises such capricious components as galvanometer, controlled heating winding and radiation energy indicator.

SUMMARY OF THE INVENTION

The principal object of the present invention is to provide a method of measuring the asphalt pavement temperature, that should comprise a step of imparting to the air used as heat-carrier the average asphalt pavement temperature and to provide a device implementing this method and that should comprise a means imparting said temperature to the air, the method and the device being simultaneously simplified.

SUMMARY OF THE INVENTION

It is an object of the present invention is to provide a method of measuring the asphalt pavement temperature and a device for implementing the same, that ensure a higher confidence of temperature measurement results.

Another object of the present invention is to provide a simplified method of temperature measurement and a device for implementing the same.

With these and other objects in view there is proposed a method of measuring the asphalt concrete pavement temperature, that comprises the measurement of temperature of air used as a heat-carrying agent, wherein, according to the invention, the air is drawn through the pavement prior to measuring its temperature.

With these and other objects in view there is also proposed a device for measuring the asphalt pavement temperature, comprising a hollow, thermally isolated chamber having a temperature meter installed thereinside, wherein, according to the invention, the chamber is made through and has a means for drawing air through asphalt pavement on one of its end faces.

Due to such a design of the device the confidence of measurement results of the asphalt pavement temperature increases sharply. This is explained by the fact that during the filtration or drawing of the air through the entire layer thickness of the asphalt pavement it passes through the pores of the asphalt, and therefore carried an integrated and averaged information about the temperature of the pavement body, and not only of its surface at the instant of measuring the temperature. At the same time the method and the device are simple.

It is advisable that in the proposed method the air filtration through the asphalt concrete pavement to performed by vacuum treatment of a pavement area isolated from the environment.

Such an embodiment is the most simple one as to its implementation.

It is also advisable that in the device for measuring the asphalt concrete pavement temperature the means for air filtration through the pavement be made as an exhaust blower whose impeller is arranged inside the chamber in close vicinity to that chamber end face where the blower is installed.

Such a design is very efficient since it provides a stability of air filtration through the pavement, which contributes to the confidence of measurement results, and is rather simple in design.

Furthermore, it is advisable that in the device for measuring the asphalt pavement temperature the means for air filtration through the pavement be made as a vacuum piston pump provided with a receiver whose inner space of the chamber through a controllable valve.

Due to such a design the device is compact, has a simple construction, is simple and reliable in service.

These and other objects and advantages of the present invention will become fully apparent from the following description taken in conjunction with the accompanying drawings, wherein:

BRIEF DESCRIPTION OF THE DRAWINGS

FIG. 1 is a schematic elevation sectional view of a device for measuring the asphalt pavement temperature according to the present invention;

FIG. 2 is a diagram of a control circuit of the electric motor driving a blower impeller of the device of FIG. 1;

FIG. 3 is a diagram of a control circuit for a temperature indicator of the device of FIG. 1.

DESCRIPTION OF THE PREFERRED EMBODIMENTS

Figure 4:
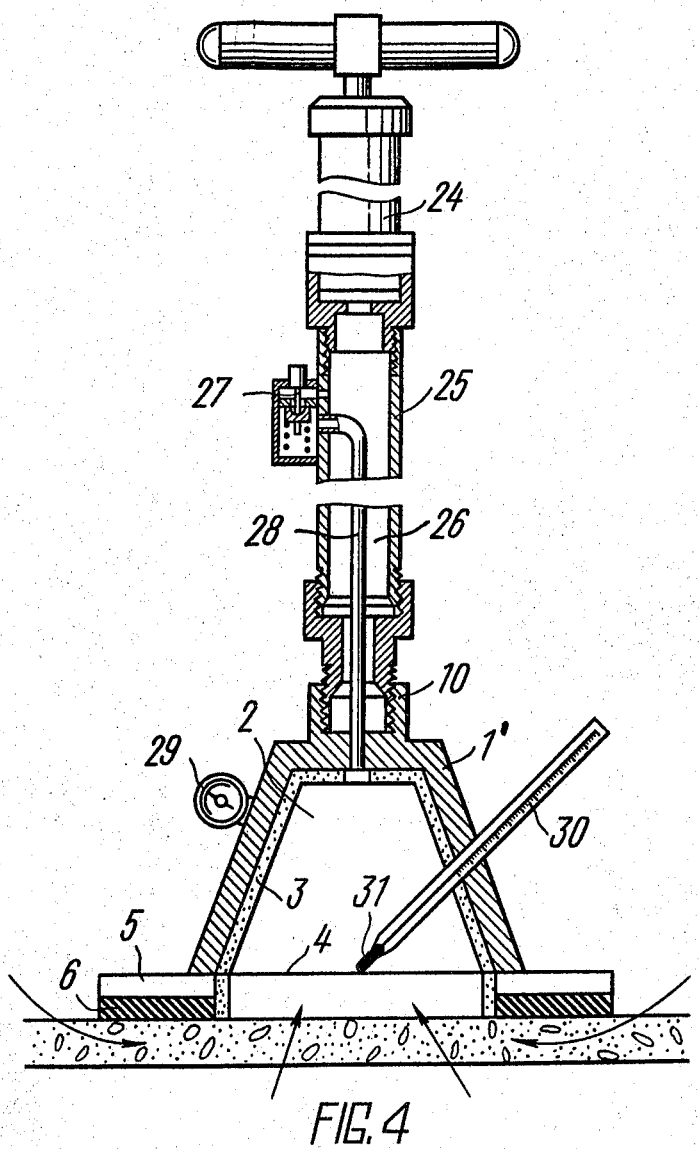
FIG. 4 is a schematic elevation sectional view of another embodiment of the device.

The method of measuring the asphalt pavement temperature in accordance with the present invention is as follows.

The temperature of an asphalt pavement is detected from the temperature of air that is a heat-carrying agent. In order to obtain confidential data about the asphalt pavement temperature air is filtered through the pavement, and then its temperature is measured.

During the filtration or, in other words, the movement of the air through the pavement it passes through the pores of the entire layer thickness of the asphalt pavement and carries an integrated average information about the temperature across the thickness of the pavement, but not only at its surface at the instant the temperature is measured.

The air filtration through the pavement is provided by vacuum treatment of a pavement area isolated from the environment. As a result, a pressure above this surface area becomes lower than that inside the pavement and in the environment. The air starts to move from the region of higher pressure to the region of lower pressure due to this pressure difference. The air that was inside the pavement has already the temperature of the latter while the air passing therethrough acquires it. The uniform and low-speed air flow has a constantly temperature that corresponds to the average asphalt pavement temperature.

It should be noted that the air filtration through the asphalt layer can be also be provided by producing an elevated air pressure over the pavement area or, in other words, by its forced pumping through the pavement.

The physical basis making the proposed method to be feasible with the desired effect is the fact that asphalt concrete is a porous material.

From the viewpoint of this property one distinguishes dense mixtures possessing a residual porosity of 3 to 5% and porous mixtures with a residual porosity of 5 to 10%. The hot asphalt concrete sharply changing its properties according to the temperature is most widely accepted in road and airfield construction. The temperature range from 70° C. to 160° C. is most reasonable for forming the desired structure of the asphalt concrete. The essence of the compaction process consists in that mineral particles are brought closer together under the effect of mechanical forces acting upon the asphalt paving mixture being compacted, and this process is accompanied by a reduction in the porosity. At the same time the entrapped air is partially dislodged while the free bitumen filling asphalt concrete pores is re-distributed to a certain degree. The residual porosity of the dense asphalt concrete should be within 3 to 5% by volume. This porosity is the sum of the total volume of intergranular spaces not filled with bitumen and the total volume of pores contained in mineral aggregates. When the porosity is discussed as one of the elements of the asphalt concrete structure, the attention should be paid to the intercommunicating portion of the pore space. It is a part of the whole porous space of the asphalt concrete referred to as the residual porosity. Thus, we consider the asphalt concrete as a porous medium whose pores contain a gas having a temperature equal to the ambient temperature. The problem of the invention is to separate the gas from the porous medium and then to measure the temperature thereof outside this layer. In any porous medium the system of pores forms a very complex surface which can be hardly characterized geometrically and described mathematically. However, the movement of a gas in a porous medium can be easily followed with the use of the method of electrohydraulic analogies.

Thus, when a vacuum is produced over a certain area of the asphalt mixture surface, the gas moves always from the inner layers of the mixture to the vacuum region, i.e. to the surface of the road pavement. The gases leaving the mixture layer will have the average temperature value of the asphalt concrete temperature.

The device for measuring the asphalt concrete pavement temperature, implementing the proposed method, has the following construction. Referring to the accompanying drawings and, in particular, to FIG. 1, the device comprises a hollow chamber 1 made as a frustum. The chamber 1 is made with an inner space 2 and of a gas-tight material. The chamber in particular of a metal, is thermally insulated from the ambient air and temperature thereof by a lining 3 of a foamed plastic.

Installed in the widened portion of the chamber 1 on an end face 4 thereof is a supporting flange 5 having a sealing disc 6 with annular grooves 7 forming a labyrinth seal on the supporting side, i.e. on the side facing the pavement. The disc 6 should be preferably made of a resilient vacuum rubber. A resistance thermometer 8 that is the temperature meter is mounted in the inner space 2 of the chamber 1 along its axis in the zone of the supporting flange 5, the resistance thermometer 8 being electrically coupled with a power supply source—a storage battery 9. Mounted on an end face 10 of the chamber 1 is a means for effecting air filtration through the pavement, made as an exhaust blower 11. An impeller 12 is arranged in the narrowed portion of the chamber 1 in close vicinity to an end face 10. The impeller 12 is connected with a direct-current electric motor 14 by means of a shaft 13, and the direct-current electric motor 14 is, in turn, electrically connected with the storage battery 9. The casing of the electric motor 14 is installed inside a sleeve 15 mounted on a bracket 16 linked rigidly with the casing 1 and which simultaneously is a handle where an instrument board 17 carrying temperature indicators and an electric motor tachometer (not shown) is installed.

The control circuit of the electric motor 14 illustrated in FIG. 2 comprises, in addition to the storage battery 9, a Zener diode 18 connected in parallel with the electric motor 14, and an adjusting resistor 19. Furthermore, the circuit comprises two on-off switches 20. It should be noted that it is preferable to use as a drive of the impeller 12 an electric series-wound motor having a "soft" operating characteristic, i.e. the relationship between the number of revolutions and the torque, that follows an exponential law.

Referring now to FIG. 3, the control circuit of the temperature indicator comprises a measuring bridge circuit 21 having an arm where the resistance thermometer 8 is inserted, the resistance thermometer 8 is coupled with a linear amplifier 22. A correcting resistor 23 linearizing the readings of the temperature indicator, is connected across the output of the linear amplifier 22 and the resistance thermometer 8.

In accordance with another embodiment of the device for measuring the asphalt pavement temperature implementing the above method, the means for providing the air filtration through the pavement is made as a vacuum piston pump 24 (FIG. 4) with a receiver 25 arranged on the end face 10 of the chamber 1'. An inner space 26 of the receiver 25 communicates with the inner space 2 of the chamber 1 through a controllable spring-loaded valve 27 and a pipe 28. Installed in the chamber 1 is a vacuum gauge 29 communicating with the inner space 2 of the chamber 1. Provided in the wall of the chamber 1 is a port where a mercurial thermometer 30 is tightly mounted so as to have a mercurial bulb 31 arranged along the axis of the chamber 1 in the zone of the supporting flange 5 thereof.

When the device according to the first embodiment of the invention is placed in operation, it is mounted on the surface of the road asphalt pavement so that the rubber sealing disc 6 (FIG. 1) isolates the inner space 2 of the chamber 1 from the environment and prevents the air leakage into the chamber 1 through gaps between it and the asphalt pavement. Then the electric motor 14 having the impeller 21 installed on the shaft 13 is switched on. The impeller 12 starts pumping the air out from the inner space 2 of the chamber 1. A pressure in the inner space of the chamber, becomes lower than the pressure of the air in the asphalt paving layer. The air starts to move from the higher-pressure zone to the lower-pressure zone, i.e. into the inner space of the chamber. Since the air inside the hot asphalt layer has the temperature of the material composing the layer, when leaving the layer, it will also have a temperature close to the average temperature of the asphalt layer. Such an air movement will be continuous, therefore the temperature of the air flow near the pavement surface will be maintained continuously and will be equal to the average temperature of the asphalt concrete layer. The resistance thermometer 8 located near the pavement surface is heated by the gas flow and, thus, measures the average temperature of the asphalt pavement.

The voltage proportional to the temperature being measured is derived from the output of the linear amplifier 22 and is applied through the correcting resistor 23 to the winding of the resistance thermometer 8 and to the input of the amplifier 22, whereby the output voltage is practically proportional to the pavement temperature being measured. The readings of the resistance thermometer 8 are taken from the indicator arranged on the instrument board 17.

The device according to the second embodiment discussed hereinabove operates as follows. The device is mounted on the surface of the road asphalt pavement so that the rubber sealing disc 6 (FIG. 4) isolates the inner space 2 of the chamber 1 from the environment and prevents air leakage into the inner space of the chamber 1 through gaps between it and the asphalt pavement. A vacuum is developed in the receiver 25 by the vacuum piston pump 24, then the receiver 25 is communicated through the controllable valve 26 and the pipe 27 with the inner space 2 of the chamber 1, causing a vacuum inside the latter. The pressure in the inner space 2 of the chamber 1 is monitored by means of the vacuum gauge 29 and should not fall below 0.9 atm. Due to the pressure difference the air starts to move from the higher-pressure zone of the asphalt pavement to the lower-pressure zone, i.e. into the inner space 2. The air that was inside the pavement had already the temperature thereof while the air passing therethrough acquires it. The uniform and low-speed air flow has a temperature corresponding to the average value of the asphalt pavement temperature. The air temperature is read on the thermometer 30. When after a certain period of time the readings of the thermometer 30 become stable, this means that its thermal sluggishness is overcome. The temperature indicated then substantially constant and is a real average temperature of the asphalt pavement.

While particular embodiments of the invention have been shown and described, minor modifications in the method of measuring the asphalt concrete pavement temperature and in the construction of the device implementing this method will be apparent to those skilled in the art and therefore it is not intended that the invention be limited to the disclosed embodiments or to the details thereof and the departures may be made therefrom within the spirit and scope of the invention as defined in the claims.

The method claimed provides a higher accuracy of measurement of the asphalt pavement temperature as compared with that provided by the prototype and for the first time makes it possible to obtain the actual temperature of the asphalt concrete pavement rather than that of its surface as it has been earlier.

The device implementing the present method is of a simple construction, reliable in service and provides a high accuracy of temperature measurement.

What is claimed is:

1. A method of determining the temperature internally of a porous, aggregate material in a pavement of a road comprising, confining a given area of a surface of an asphalt road pavement while still in a heated state after paving of the road and comprising an aggrevate material which is porous and isolating said area from the ambient atmosphere and simultaneously defining over said area of the surface an enclosed volume of space thermally isolated from the ambient atmosphere, applying a vacuum to said space for drawing into said enclosed volume of space from internally of the pavement aggregate material gases entrained in pores of the porous aggregate material, and sensing the temperature of the gases drawn into said volume of space with a temperature sensor within said enclosed space, while still in a heated stated after paving of the paving of the road and thereby to ascertain the temperature of the asphalt pavement.

2. Apparatus for determining the temperature internally of an asphalt pavement material applied to a roadway and while still in a heated state comprising, means for confining a given area of a surface asphalt pavement material applied on a roadway while still in a heated state and isolating it from the ambient atmosphere, means connected to the first-mentioned means for simultaneously defining an enclosed volume of space over said surface while isolating it and thermally isolating it from the ambient atmosphere, vacuum-applying means for applying a vacuum to said volume of space while said roadway surface asphalt pavement material is in a heated state for drawing into said enclosed volume of space from internally of the asphalt pavement material gases entrained in pores and voids of the material, and temperature sensor means within said enclosed space for sensing the temperature of the gases drawn into said volume of space.

3. Apparatus for determining the temperature internally of an asphalt pavement material applied to a roadway according to claim 2, in which said vacuum-applying means comprises means for exhausting air from said volume of space and developing a partial vacuum therein.

4. Apparatus for determining the temperature internally of an asphalt pavement material applied to a roadway according to claim 2, in which said vacuum-applying means comprises a vacuum pump for developing a partial vacuum in said volume of space over said surface so that gases entrained in the asphalt material escape into said volume of space.

* * * * *